United States Patent
Sagiv

(10) Patent No.: US 6,182,656 B1
(45) Date of Patent: Feb. 6, 2001

(54) DEVICE AND METHOD FOR TRANSFORMING A UNIDIRECTIONAL FLOW INTO AN OSCILLATING FLOW EMPLOYED IN AN ARTIFICIAL RESPIRATION SYSTEM

(76) Inventor: Ovadia Sagiv, POB 7090, Tel-Aviv 61070 (IL)

( * ) Notice: Under 35 U.S.C. 154(b), the term of this patent shall be extended for 0 days.

(21) Appl. No.: 09/190,148

(22) Filed: Nov. 12, 1998

Related U.S. Application Data

(60) Provisional application No. 60/065,795, filed on Nov. 14, 1997.

(51) Int. Cl.[7] .................................................. A61M 16/00
(52) U.S. Cl. .............................. 128/204.18; 128/202.12
(58) Field of Search ................. 128/204.18, 202.12, 128/205.26, 204.21; 601/6, 9, 41–43, 44; 600/21, 22

(56) References Cited

U.S. PATENT DOCUMENTS

| | | |
|---|---|---|
| 3,658,443 | 4/1972 | Fumagalli . |
| 4,621,621 | 11/1986 | Marsalis . |
| 4,928,674 * | 5/1990 | Halperin et al. ..................... 128/30.2 |
| 4,930,498 | 6/1990 | Hayek . |
| 4,971,042 * | 11/1990 | Lerman .............................. 128/30.2 |
| 4,982,735 | 1/1991 | Yagata et al. . |
| 5,056,505 * | 10/1991 | Warwick et al. ..................... 128/30.2 |
| 5,299,599 | 4/1994 | Farmer et al. . |
| 5,988,166 * | 11/1999 | Hayek ............................ 128/205.26 |

* cited by examiner

Primary Examiner—John G. Weiss
Assistant Examiner—Teena Mitchell
(74) Attorney, Agent, or Firm—Jerome D. Jackson

(57) ABSTRACT

An artificial respirator employs rotating chambers to modulate pressure from a unidirectional fluid source. The chambers are defined by a core rotating in a shell. The core includes an internal divider and a back wall. The core also includes a shaft coupled to a motor. The motor is mounted on the shell via screws.

13 Claims, 12 Drawing Sheets

DEVICE AND METHOD FOR TRANSFORMING A UNIDIRECTIONAL FLOW INTO AN OSCILLATING FLOW EMPLOYED IN AN ARTIFICIAL RESPIRATION SYSTEM

BACKGROUND OF THE INVENTION

This Application claims the benefit of Application Ser. No. 60/065,795 of Ovadia Sagiv filed Nov. 14, 1997 for DEVICE ENABLING TO TRANSFORM A CONSTANT AND UNIDIRECTIONAL FLOW TO AN OSCILLATING FLOW, the contents of which are herein incorporated by reference.

FIELD OF THE INVENTION

This invention relates generally to control of fluid flow from a unidirectional source and, more particularly, to control of air pressure in a respirator employing a unidirectional air pressure source.

DESCRIPTION OF RELATED ART

Artificial respirators are known. One type of respirator induces breathing by forcing pressurized air down the patient's trachea, using an intubation tube. Although intubation is commonly employed, intubation tends to be traumatic.

Another type of respirator induces breathing by varying air pressure outside the patient's chest, while leaving the patient's mouth and nose at ambient pressure. Decades ago, this type of respirator was known as an "Iron Lung" and employed a tank in which the entire body except the head was enclosed. Since then, more portable and generally practical devices have been proposed.

U.S. Pat. No. 4,621,621 discloses a respirator jacket assembly, a source of vacuum pressure, and a valve assembly. A motor, shaft, lifter, and rocker arm cooperate to move a movable conduit to be coaxial with a fixed conduit, to put the jacket assembly in fluid communication with the vacuum source, thereby creating a negative pressure around the torso of the user, causing air to rush into the lungs. When the movable conduit is in the displaced position, the pressure within the jacket returns to ambient pressure, thereby permitting the user to exhale.

U.S. Pat. No. 4,930,498 purports to disclose a ventilator having valve that may be used to provide alternately low and high pressures. This valve is connected to separate sources of gas pressure and vacuum.

U.S. Pat. No. 4,982,735 discloses a system including a blower that supplies alternately negative and positive pressure to a dome attached to the chest of the patient. The blower is part of a circuit including an air suction valve, an air exertion valve, a release valve, two bypass valves, a negative pressure regulator, and a positive pressure regulator.

These prior systems may be characterized by either a lack of versatility or a complex construction.

SUMMARY OF THE INVENTION

It is an object of the present invention to provide a versatile pressure control mechanism that may employ a relatively simple pressure source in a respirator.

To achieve this and other objects of the present invention, in a system including a compartment and a person in contact with the compartment having an interior, an artificial respiration system comprises a device for moving fluid, the device including a fluid exit port and a fluid entrance port; a first housing defining a first hole in communication with the exit port, a second hole in communication with the interior of the compartment, a third hole in communication with the entrance port, and a fourth hole; a second housing in the first housing, the second housing defining a first chamber with a first hole, and a second hole, and a second chamber with a third hole, and a fourth hole; a driver for varying the angular displacement of the second housing relative to the first housing; a user interface for generating a first signal indicating a first pressure, a second signal indicating a second pressure, and a third signal indicating a period; and a controller that generates a driver control signal to effect a first angular displacement of the second housing depending on the first signal, and to effect a second angular displacement of the second housing depending on the second signal.

According to another aspect of the present invention, there is a method for a system including a compartment and a person in contact with the compartment having an interior, a device for moving fluid, the device including a fluid exit port and a fluid entrance port; a first housing defining a first hole in communication with the exit port, a second hole in communication with the interior of the compartment, a third hole in communication with the entrance port, and a fourth hole; and a first cell with a first hole, and a second hole. The method comprises generating a first signal indicating a first pressure, a second signal indicating a second pressure, and a third signal indicating a period; generating a control signal to effect a first angular displacement of the first cell, relative to the first housing, depending on the first signal, and to effect a second angular displacement of the first cell depending on the second signal; and rotating the first cell in response to the control signal.

The accompanying drawings which are incorporated in and which constitute a part of this specification, illustrate embodiments of the invention and, together with the description, explain the principles of the invention, and additional advantages thereof. Throughout the drawings, some structures had been drawn out of scale in order to more clearly show certain feature of the preferred embodiment. Throughout the drawings, corresponding parts are labeled with corresponding reference numbers.

DESCRIPTION OF THE PREFERRED EMBODIMENTS

Figure 1:
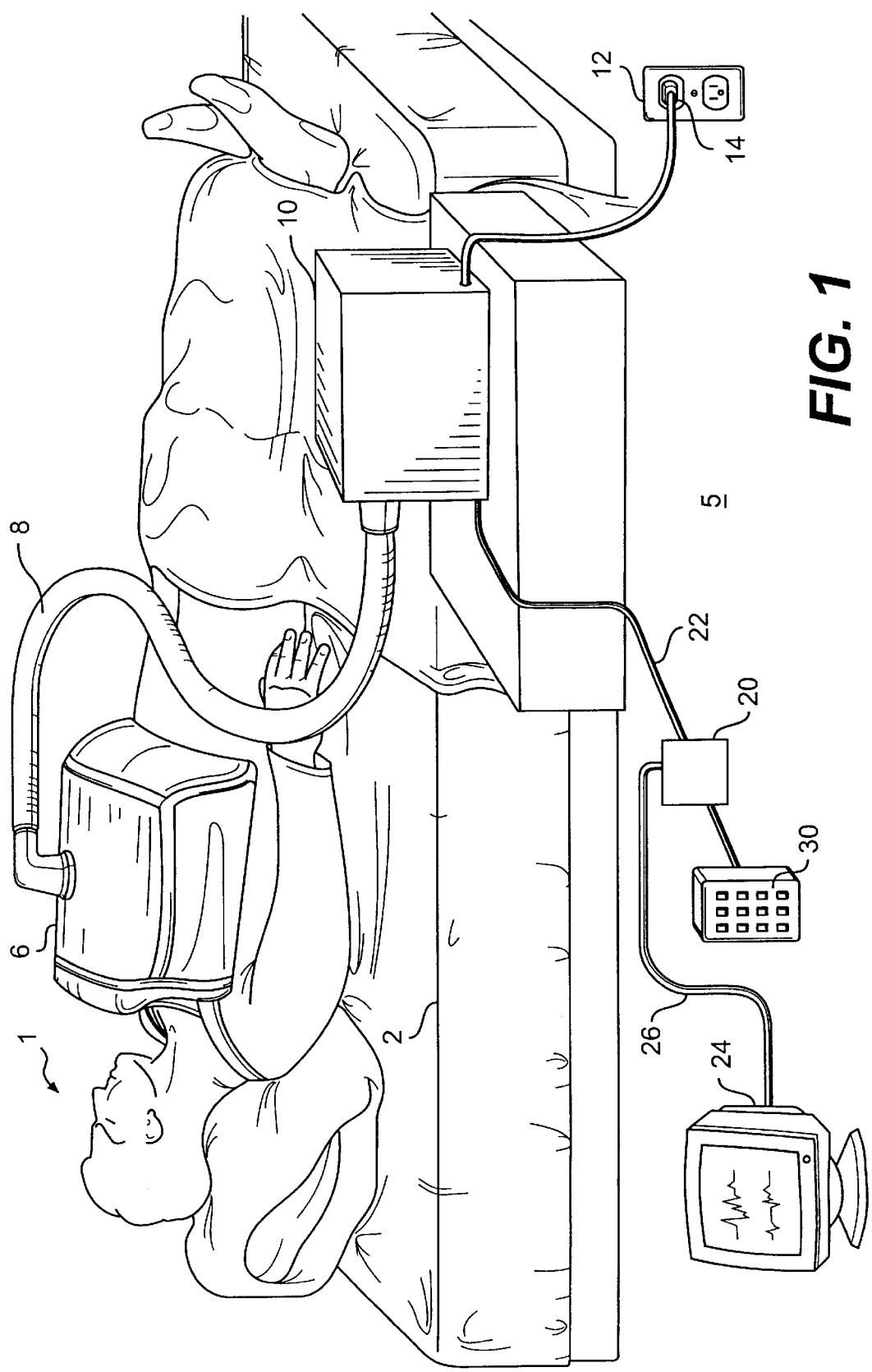
FIG. 1 is a diagram showing a preferred artificial respiration system in overview.

FIG. 1 shows a hospital room employing a respirator system in accordance with a preferred embodiment of the present invention. Patient 1 rests on bed 2. Patient 1 wears a compartment 6 that defines a substantially pressure tight interior chamber 9 (see FIG. 7) over the chest of Patient 1. Compartment 6 may be a device such as the respirator jacket assembly disclosed in U.S. Pat. No. 4,621,621 or the dome disclosed in U.S. Pat. No. 4,982,735.

A mechanical assembly inside mechanical kiosk 10 effects pressure variations in the chamber in compartment 6, via conduit 8, as described in more detail below. Motors in mechanical kiosk 10 receive a power signal via plug 14 from wall socket 12, which may supply 90–240 VAC in either a 60 Hz, 50 Hz, or 400 Hz power signal.

Electronics kiosk 20 is coupled to a keyboard 30 via a cable or a remote control. A microprocessor-based controller is inside electronic kiosk 20.

CRT 24 receives signals from electronics kiosk 20 via cable 26, allowing medical personnel to monitor and control the respiratory cycle of patient 1.

Figure 2A:
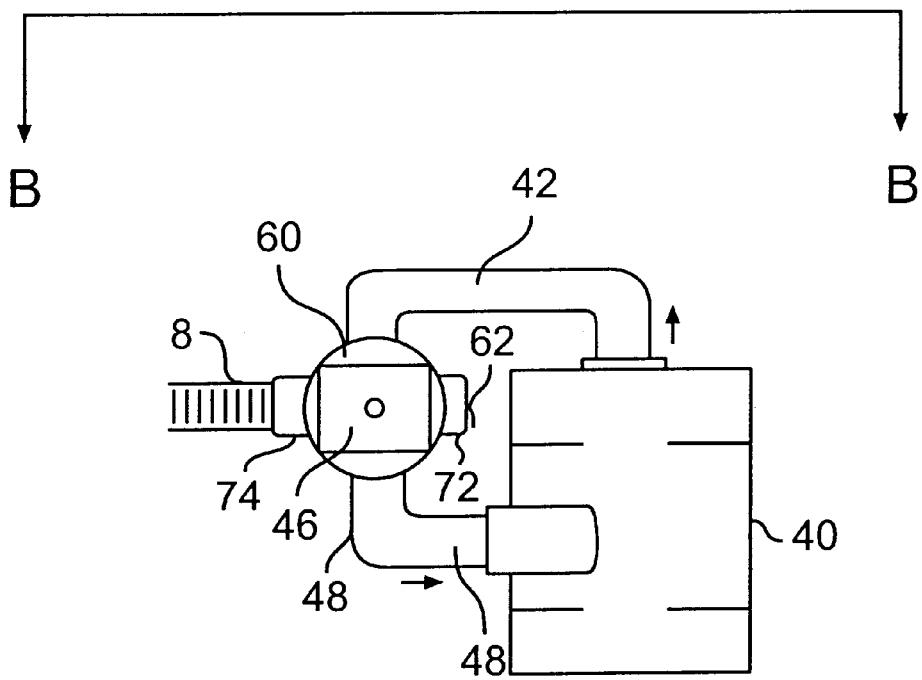
FIGS. 2A and 2B are diagrams emphasizing certain mechanical elements in the preferred system.

FIG. 2A shows some of the elements inside of mechanical kiosk 10. Blower 40 is a 400 Watt, 240 Volt, bypass blower. Blower 40 may be a type E blower available from AMETEK Technical Motor Divisions, 627 Lake Street, Kent, Ohio 44240.

Stepper motor 46 drives a mechanical element inside of Shell 60, to modulate an air current flowing from blower 40 through conduit 42 to adapter 74 and hose 8, while blower 40 is vented through conduit 48 and hole 62 in shell 60, as described in more detail below. Stepper motor 46 may be a 2-phase Stepper Motor that moves 0.9°/Step, in response to a pulse signal. Motor 46 may be a model CSK 266-BT available from Oriental Motor General.

Figure 2B:
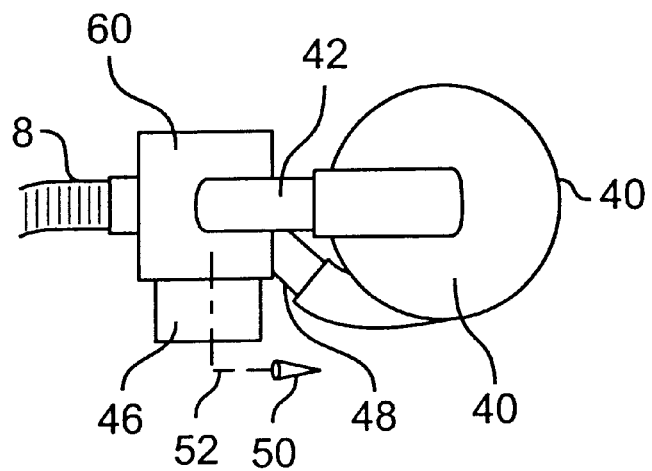

As shown in FIG. 2B, a photo diode 50 generates a signal to detect when motor shaft 52 is at the 0° orientation.

Figure 3:
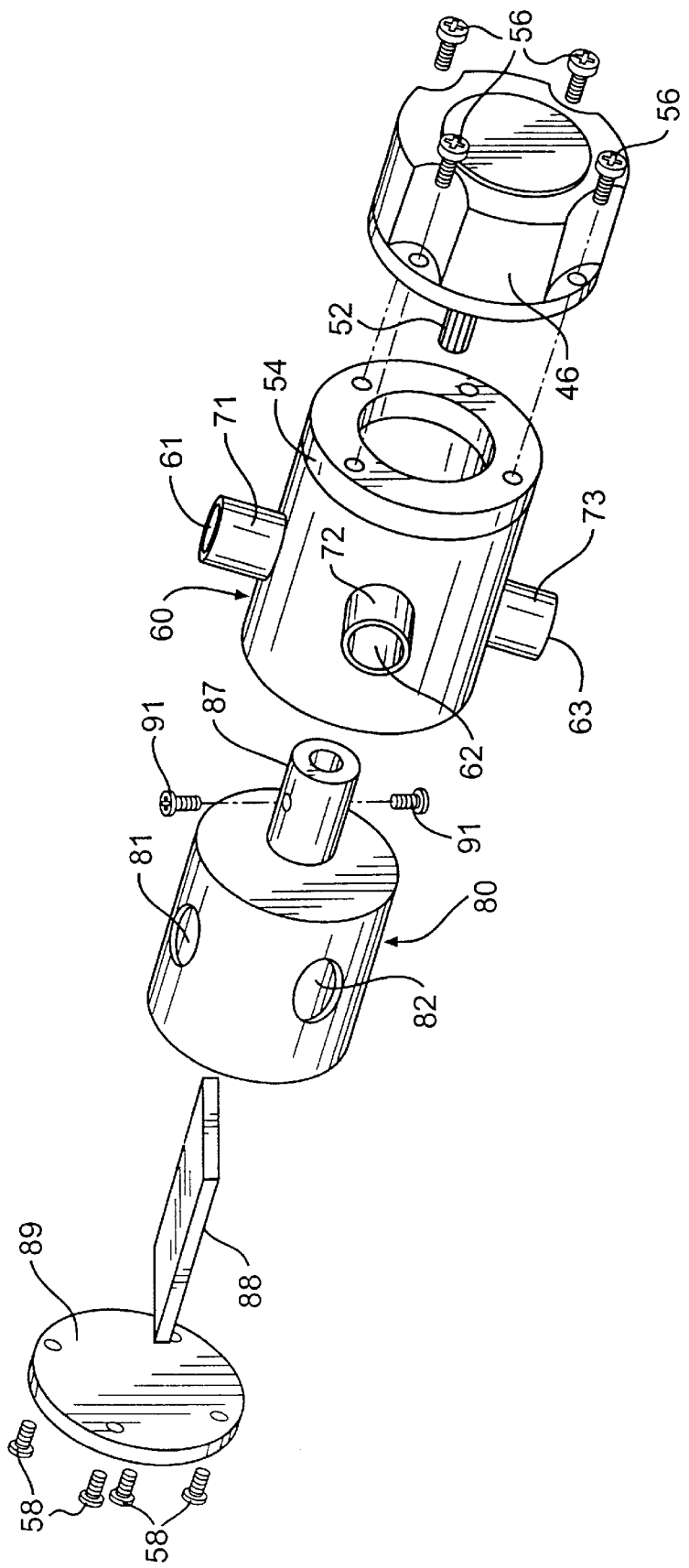
FIG. 3 is a diagram showing some of the elements of FIG. 2A in more detail.

FIG. 3 shows an exploded view including motor 46, shell 60, hose and conduit adapters 71, 72, 73, and 74, and mechanical elements in shell 60. Mechanical elements in shell 60 include a core 80 having an internal divider 88 and a back wall 89. Core 80 includes shaft 87, coupled to motor 46 via screws 91. Motor 46 is mounted on shell 60 via mounting plate 54 and screws 56. Core 80 is mounted to rotate inside shell 60. The external diameter of core 80 is fitted to the internal diameter of shell 60 by a close tolerance. Seals can be added if necessary.

It is presently preferred that elements 54, 71, 72, 73, and 74 be either integrally formed or separate from shell 60. It is preferred that shaft 87 be integrally formed with core 80. It is preferred that divider 88 be either integrally formed or separate from core 80.

Opening 64 is in communication with interior chamber 9 via adaptor 74 and conduit 8.

Figure 4:
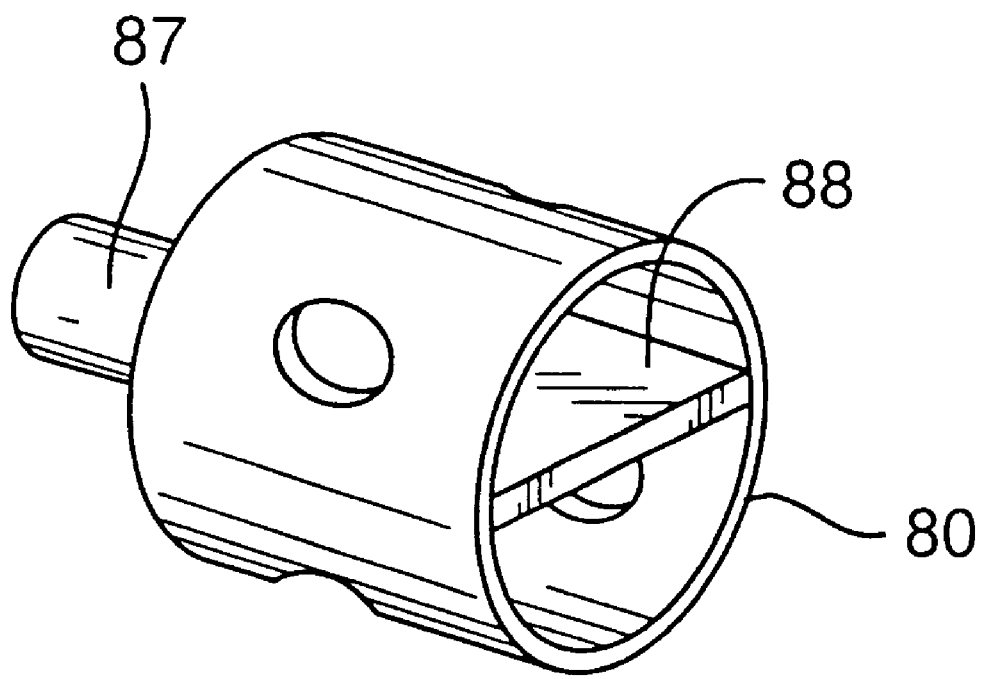
FIG. 4 is a perspective view of one of the elements of FIG. 2A in more detail.

FIG. 4 is a perspective showing of core 80.

Figure 5:
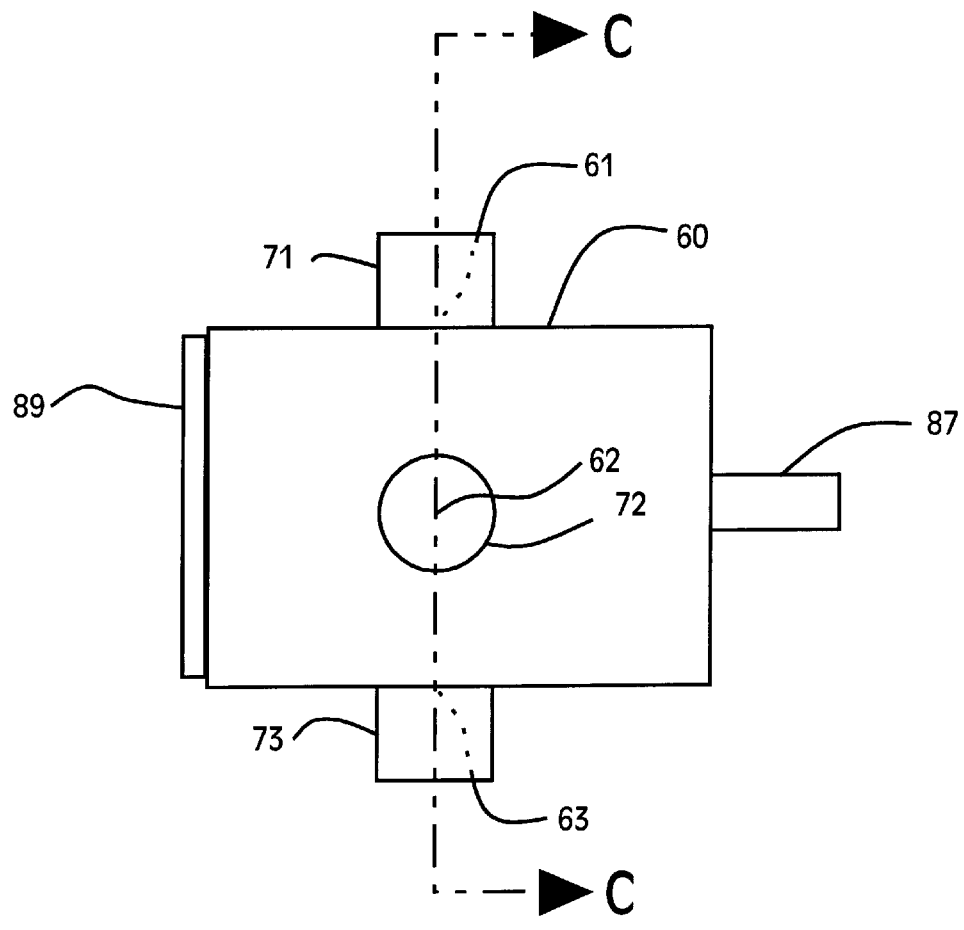
FIG. 5 is a plan view showing one of the elements of FIG. 2A in more detail.
Figure 6A:
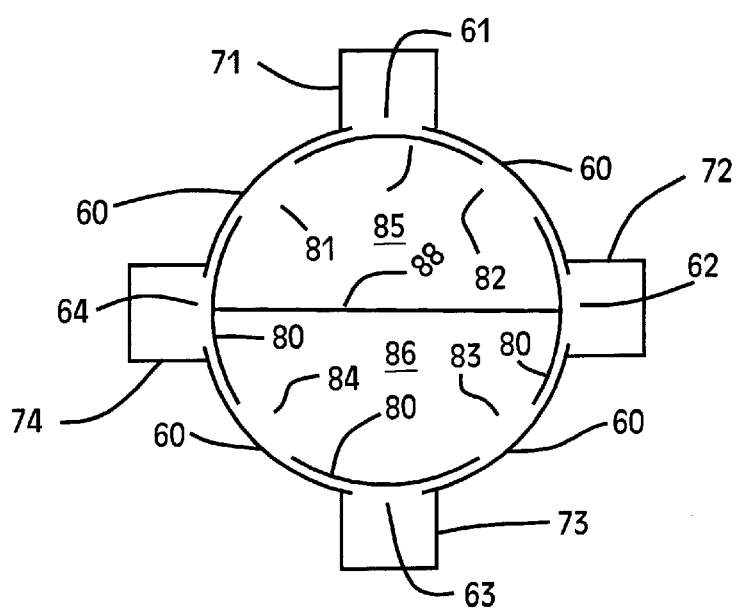
FIG. 6A is a cut-away view taken along the line C—C in FIG. 4, at a certain point in time.

FIG. 5 is a side view of Shell 60, and FIG. 6A is a cutaway view taking along the line C—C in FIG. 5. Shell 60 has round openings 61, 62, 63, and 64. Opening 61 is connected to the pressure side of blower 40 depicted in FIGS. 2A and 2B via adapter 71 and conduit 42 depicted in FIG. 2A and 2B, and opening 63 is connected to the vacuum side of blower 40 via adapter 73 and conduit 48. Opening 64 is connected to compartment 6 via adapter 74 and conduit 8. Opening 62 is connected to ambient air pressure via adapter 72.

In the exemplary system, shell 60 defines a length of approximately 75 mm. Adapters 71, 72, 73, and 74 each define a diameter of approximately 30 mm.

Figure 6B:
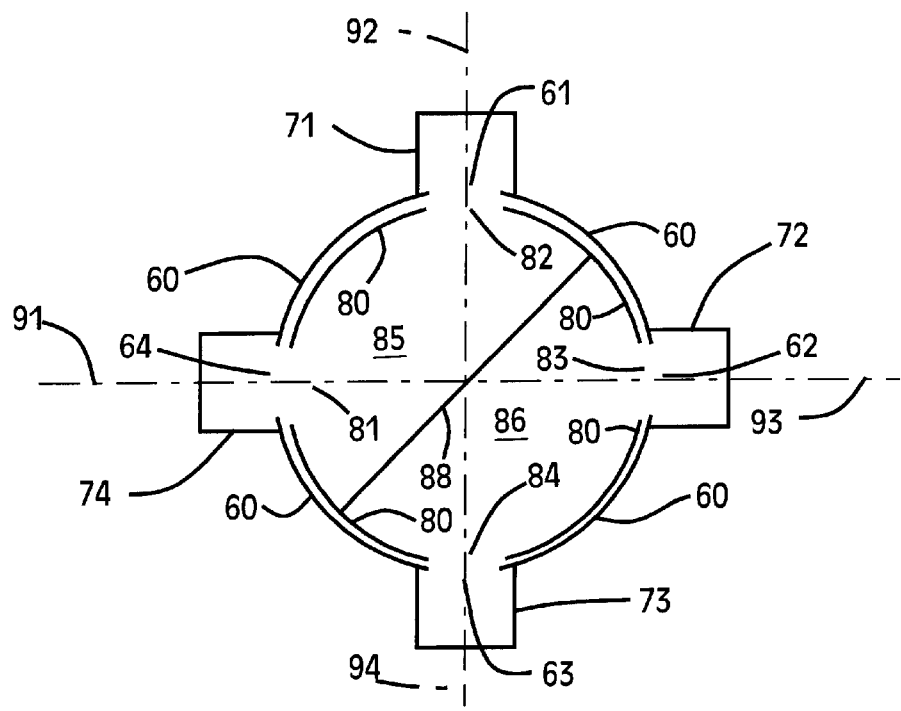
FIG. 6B is a cut-away view taken at a subsequent time from the time of FIG. 6A.

Core 80 defines chambers 85 and 86. Chamber 85 is closed except for round holes 81 and 82. As shown in FIG. 6B, an angle of 90° is defined by a line 91 normal to hole 81 and a line 92 normal to hole 82.

Chamber 86 is closed except for round holes 83 and 84. An angle of 90° is defined by a line 93 normal to hole 83 and a line 94 normal to hole 84.

This arrangement of two perpendicular holes for each chamber reassures good sealing between the two chambers.

In FIG. 6B, line 91 is also normal to shell hole 64 and line 92 is normal to shell hole 61; line 93 is normal to shell hole 62 and line 94 is normal to shell hole 63.

Further, lines 92 and 93 also define a 90° angle; shell hole 61 is perpendicular to shell hole 62, and core hole 82 is perpendicular to core hole 83. Lines 91 and 94 define a 90° angle; shell hole 64 is perpendicular to shell hole 63, and core hole 81 is perpendicular to core hole 84.

When core 80 is rotatably mounted inside shell 60, holes 81, 82, 83, and 84 of core 80 may overlap holes 61, 62, 63, 64, respectively, of Shell 60, as shown in FIG. 6B.

Core's (and Shell's) four round holes diameter (d) are made to fit their common contact diameter (D) to achieve either positive flow or suction (never together), because $D \geq d\,(core)/\sin(\pi/8)$, where D is the external diameter of the core and d (core) is the diameter of each of holes 81, 82, 83, and 84.

Further $d\,(core) \geq d\,(shell)$, so that each angular displacement of core 80, relative to shell 60, tends results in a different amount of overlap between holes 81, 82, 83, 84, and holes 61, 62, 63, 64.

In the exemplary system, D is approximately 80 mm, d(core) is approximately 25 mm, and d(shell) is approximately 25 mm.

Thus, the size of all four "effective" passages is controlled by this arrangement in core 80 where a pair of perpendicular round holes is leading to each of its two chambers, enabling a complete balanced cycle every 90°, to control pressure and/or flow for all four passages by the amount of overlap between core's and shell's holes.

Further, this arrangement ensures that, regardless of the current angular displacement of core 80, the effective passages in chamber 85 will have a common size, and the two effective passages in chamber 86 will have a common size, helping to suppress noise and whistles that might exist if the effective passages had different sizes. In other words, the four effective passage ways will vary in size. Further, the four effective passageways will have a common size at any particular point in time.

In summary, using the relationship of holes 61, 62, 63, and 64 to holes 81, 82, 83, 84, respectively as an example, an extent of overlap of hole 81 with hole 61 is a first function of the angular displacement of core 80, and an extent of overlap of hole 82 with hole 62 is the first function. In other words, any effective passage way created by an overlap of holes 81 and 61 will have these same size, at a certain point in time, as any passageway created by overlap of holes 82 and 62.

Further, an extent of overlap of hole 83 with hole 63 is a second function of the angular displacement of the core 80, and an extent of overlap of hole 84 with hole 64. In other words, any effective passage way created by an overlap of holes 83 and 63 will have the same size, at a certain point in time, as the passageway created by an overlap of holes 84 and 64.

Further, the first and second functions are substantially the same, meaning that the common pair of passageway size (resulting from the hole 81–61 and hole 82–62 overlap) will also be common with the common passageway size effected by the hole 83–62 overlap and the hole 84–64 overlap.

Figure 7:
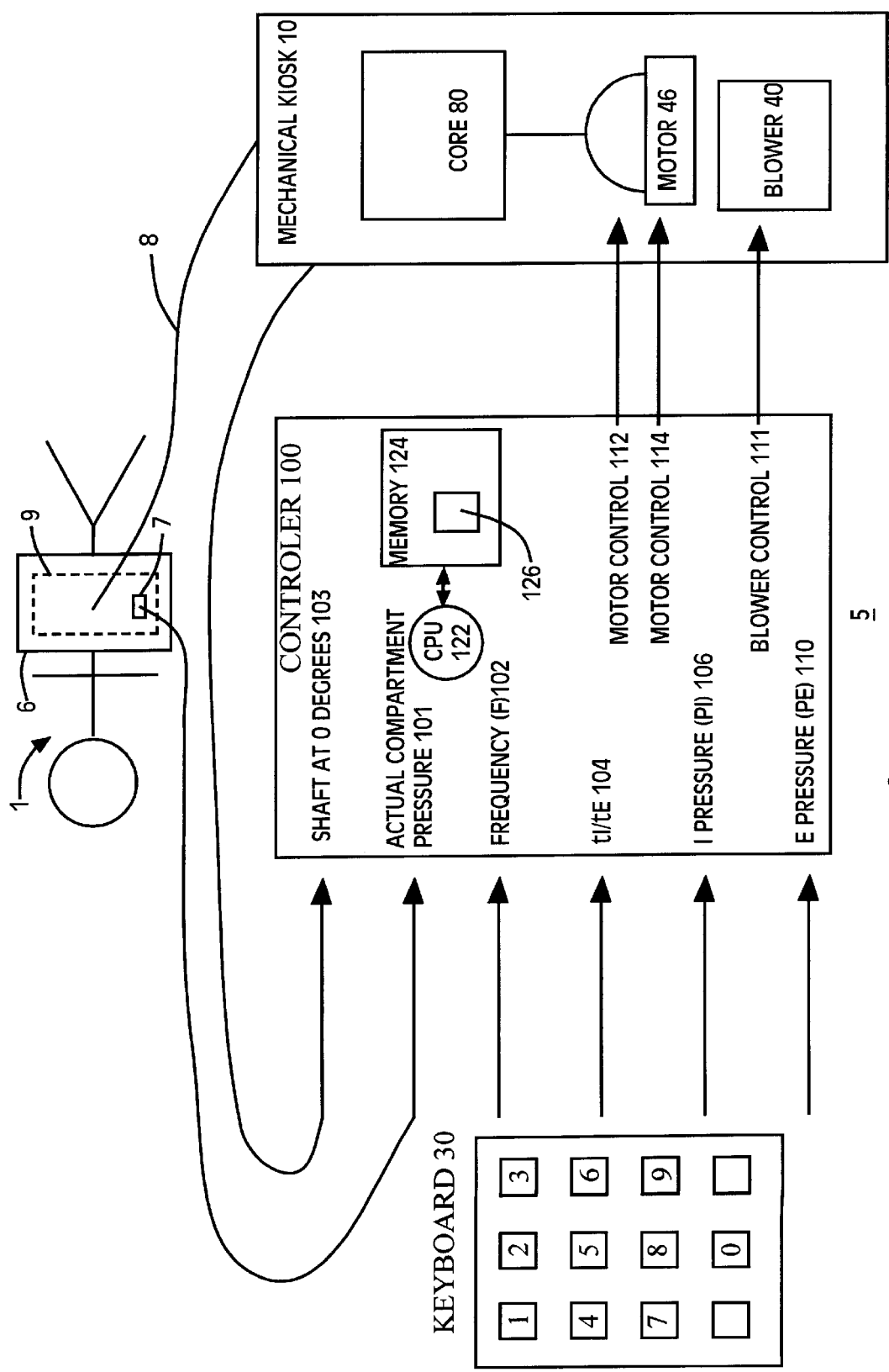
FIG. 7 is a block diagram emphasizing certain signal paths in the preferred respiration system.

FIG. 7 shows a diagram emphasizing certain signal path in the preferred respirator. Controller 100 includes central processing unit (CPU) 122 and random access memory (RAM) 124. Memory 124 stores a program 126. CPU 122 executes program 126.

Controller 100 receives various input signals from keyboard 30. These signals include a respiration frequency 102, and inspiration time to expiration time ratio 104, an inspiration pressure 106, and an expiration pressure 110. Pressure sensor 7 generates signal 101, indicating an actual pressure inside compartment 6. In response to signals 101, 102, 104, 106, and 110, controller 100 generates motor control signal 112 to cause motor 46 to rotate, and motor control signal 114 to control direction of rotation (clockwise or counterclockwise). Responsive to signals 112 and 114, motor 46 turns core 80 relative to shell 60.

Both the pressure effected to induce expiration (PE), and the pressure effected to induce inspiration (PI), may be controlled by controller 100's changing the speed (output) of blower 40 and the angular displacement of core 80. The total period (T) of the preferred system is composed of Exp time (tE) and Insp time (tI).

Because of the size and position of holes 81, 82, 83, and 84, of core 80, compartment 6 receives either positive flow or suction (never together), in an amount depending on the time that holes 81, 82, 83, 84 coincide with holes 61, 62, 63, and 64.

One side (exit or entrance at each half cycle) of blower 40 may be properly vented to the ambient medium, in order not to block its operation and ensuring the constant flow. The preferred system can deliver any amount of flow starting from zero to the maximum of blower 40, at any rate and intervals depending on the rotation speed of the core 80.

Figure 6C:
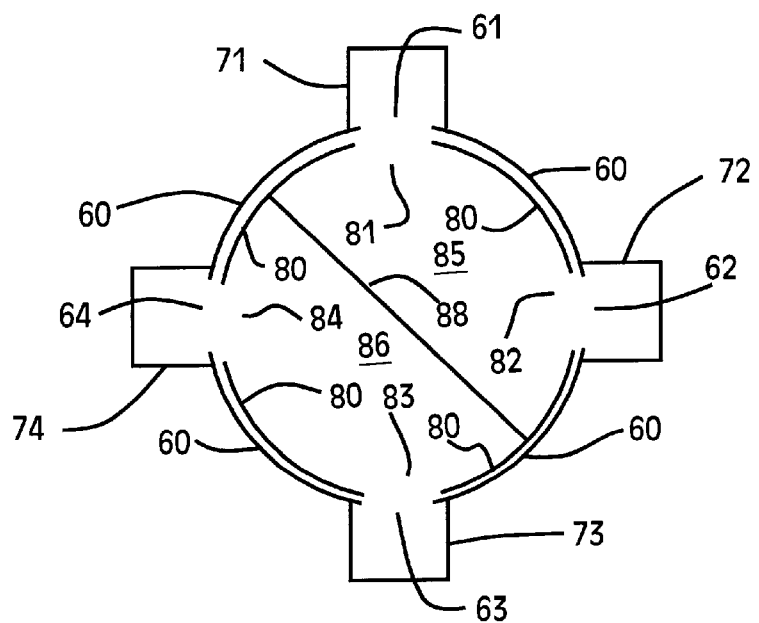
FIG. 6C is a cut-away view taken at a subsequent time from the time of FIG. 6B.
Figure 8:
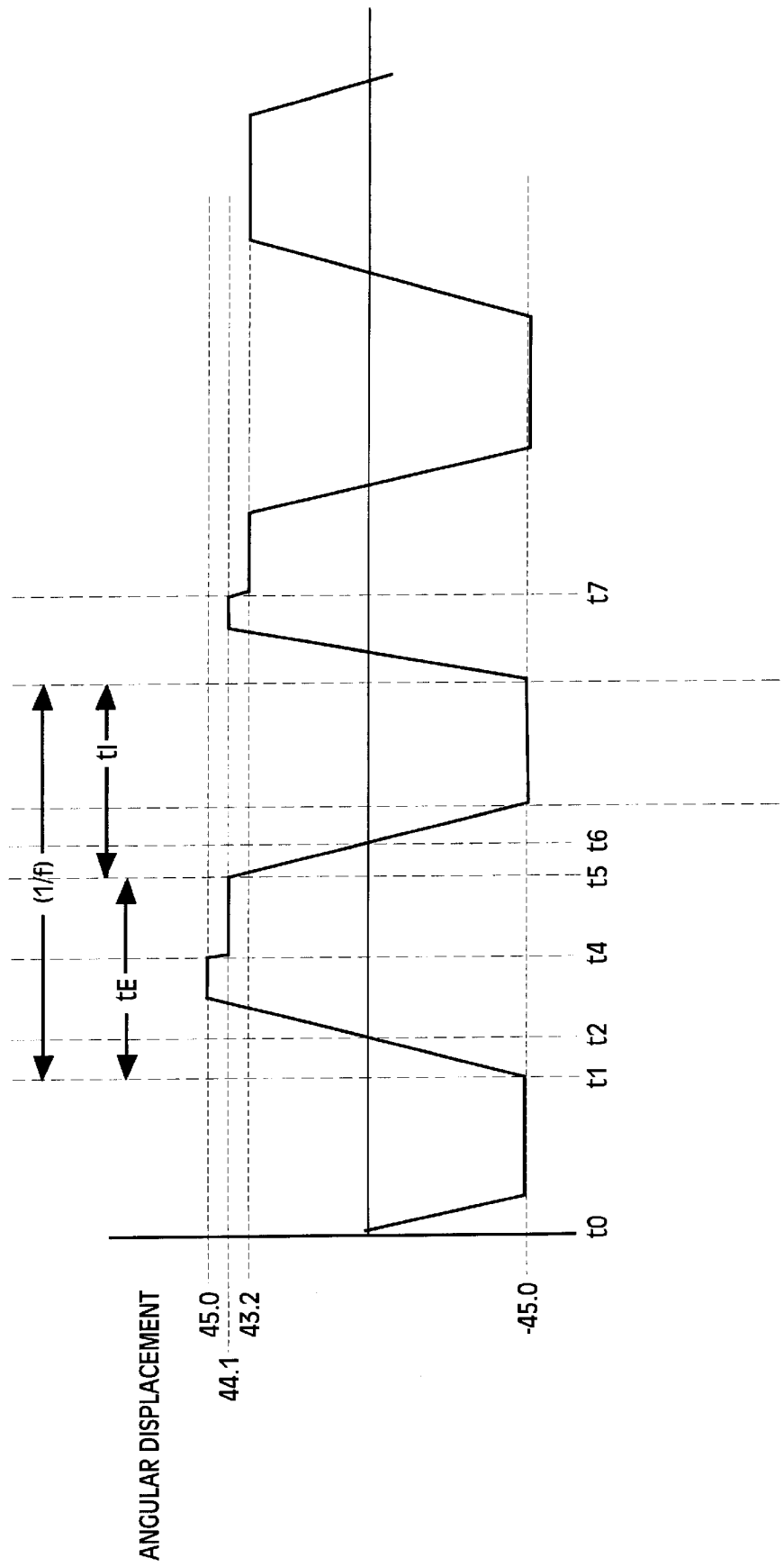
FIG. 8 is a wave form showing angular displacements effected by a process performed in the preferred respiration system.
Figure 9:
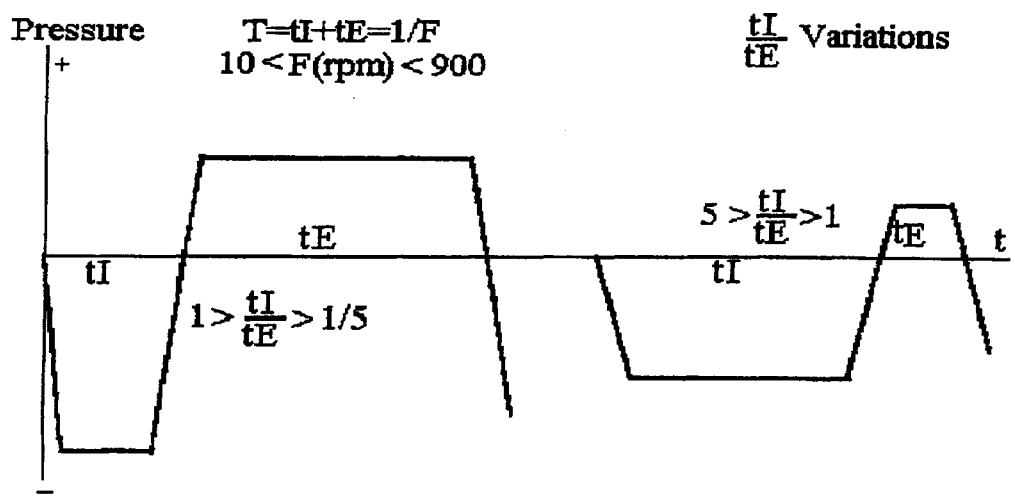
FIG. 9 is a diagram showing an operation mode of the preferred system.
Figure 10:
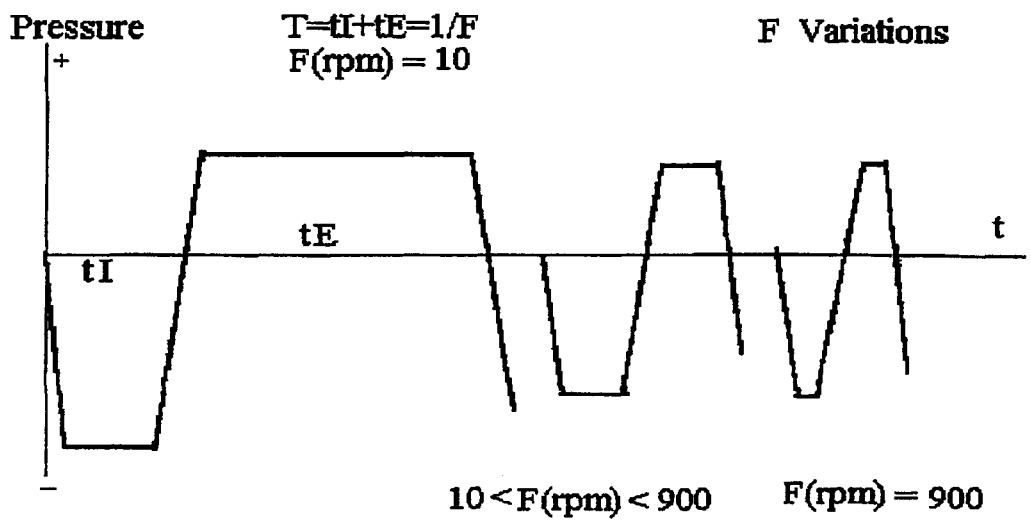
FIG. 10 is a diagram showing another operation mode of the preferred system.
Figure 11:
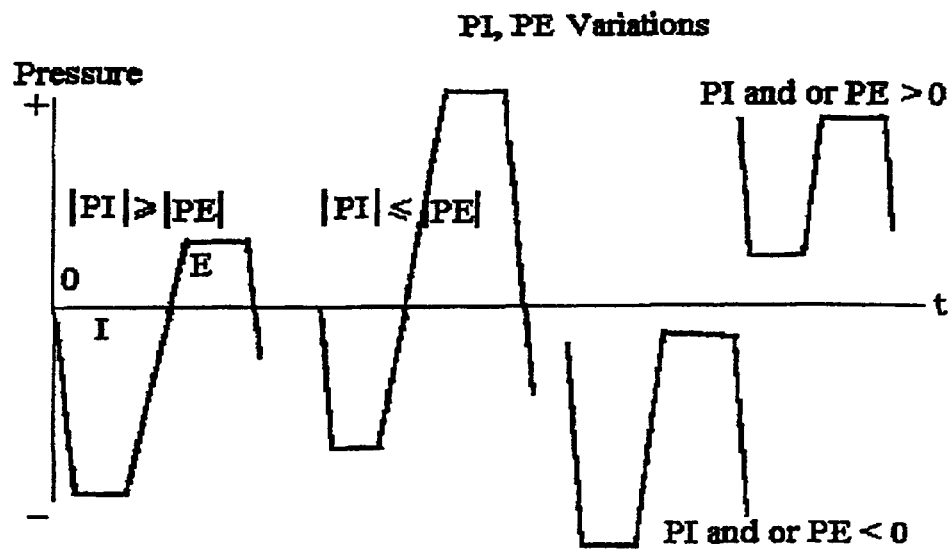
FIG. 11 is a diagram showing yet another operation mode of the preferred system.

FIG. 8 shows some angular displacements in the preferred system. At a time t0, controller 100 sets the angular displacement to −45° as shown in FIG. 6B. After waiting for an interval tI at time t1 controller 100 generates pulses in motor control signal 112, to set the angular displacement to 0° as shown in FIG. 6A and at a time t2 controller 100 generates pulses in motor control signal 112, to set the angular displacement the current value of E. The first time through the loop, E will be 45° as shown in FIG. 6C. In this example, 45° results in a pressure that is more than the programmed expiration pressure at which time controller 100 decreases the angular displacement by 0.9 at a time t4. After waiting for the interval tE, at time t5 controller 100 generates pulses in motor control signal 112, to set the angle to 0°, and at t6 generates pulses in motor control signal 112, to set to an angle of −45°.

Figure 6D:
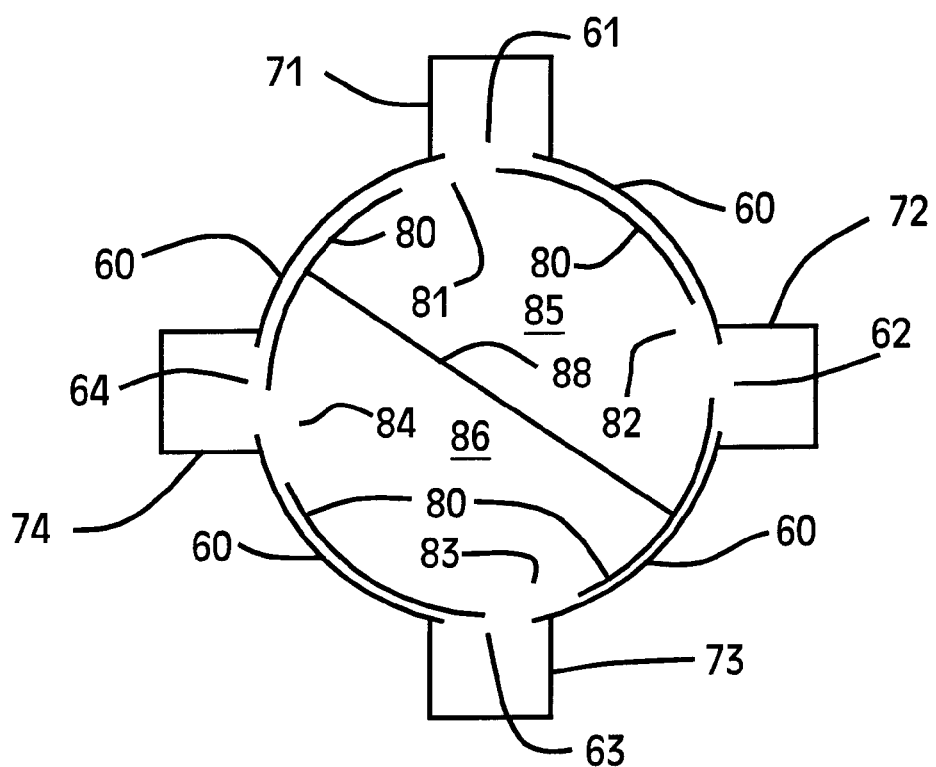
FIG. 6D is a cut-away view taken at a subsequent time form the time of FIG. 6C.

The actual pressure is still greater than the programmed expiration pressure and at t7 controller 100 again generates pulses in motor control signal 112, to reduce the angular displacement by 0.9. The expiration pressure is now equal to the programmed expiration pressure. In other words, the angle of 43.2° shown in FIG. 6D results in the appropriate passage way size to achieve this programmed expiration pressure.

In FIGS. 6A, 6B, 6C, 6D, and 8, and throughout the specification, certain angular relationships and slopes have been drawn out of scale, or otherwise exaggerated, in order to more clearly describe the operation of the preferred embodiment.

Of course, the exemplary system, including the numerical quantities, disclosed in the specification are presented by way of example only and not limitation, because the invention is defined by the claims at the end of the specification.

In summary, the preferred respiration system 5 includes blower 40, which is essentially a device for moving fluid. Blower 40 includes a fluid exit port and a fluid entrance port.

Shell 60 is essentially a housing defining a hole 61 in communication with the exit port, a hole 62, a hole 63 in communication with the entrance port, and a hole 64.

Core 80 is essentially a second housing in shell 80. Shell 80 defines a chamber 85 with a hole 81, and a hole 82 perpendicular to hole 81. Shell 80 also defines a chamber 86 with hole 83, and a hole 84 perpendicular to hole 83.

Motor shaft 52 is connected to core shaft 87, via screws 91. Thus, motor 46 is a type of driver that acts to vary the angular displacement of core 80 relative to shell 60.

Keyboard 30 is essentially a user interface for generating signal 106 indicating an inspiration pressure (a first pressure). Keyboard 30 also generates a signal 110 indicating an expiration pressure (a second pressure). Keyboard 30 also generates signal 102 indicating a respiration frequency (reciprocal of respiration period).

Controller generates pulse signal 112 to effect a first angular displacement depending on the inspiration pressure, and to effect a second angular displacement depending on the expiration pressure.

FIGS. 9–14 outline some processing modes for the what may be deemed the normal operating mode for four respiratory parameters: F, tI/tE, PI, PE. This mode uses four respiratory parameters: F, tI/tE, PI, PE. The system provides patient with programmed respiration and monitors by close loop (feedback) the four respiratory parameters. Parameters are changed during operation as required by patient.

Figure 12:
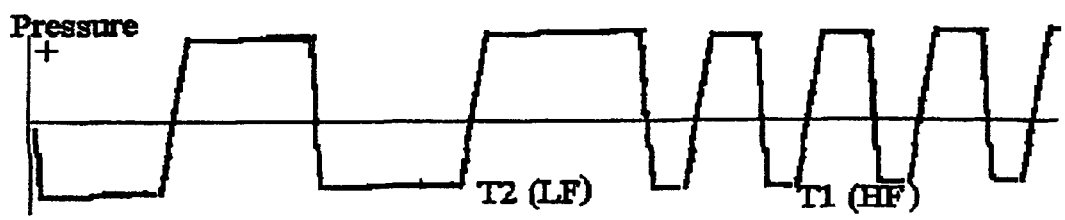
FIG. 12 is a diagram showing yet another operation mode of the preferred system.

FIG. 12 shows the dual mode. The dual mode is useful for massage action. The algorithm is to select a pair of parameter sets: F, tI/tE, PI, PE and time period for each cycle. The system provides patient with two sets of controlled respiration: one set is of High Frequency Respiration (HF) and second set is of Low Frequency Respiration (LF) while monitoring by close loop (feedback) the four respiratory parameters. Parameters are changed during operation as may be required.

Figure 13:
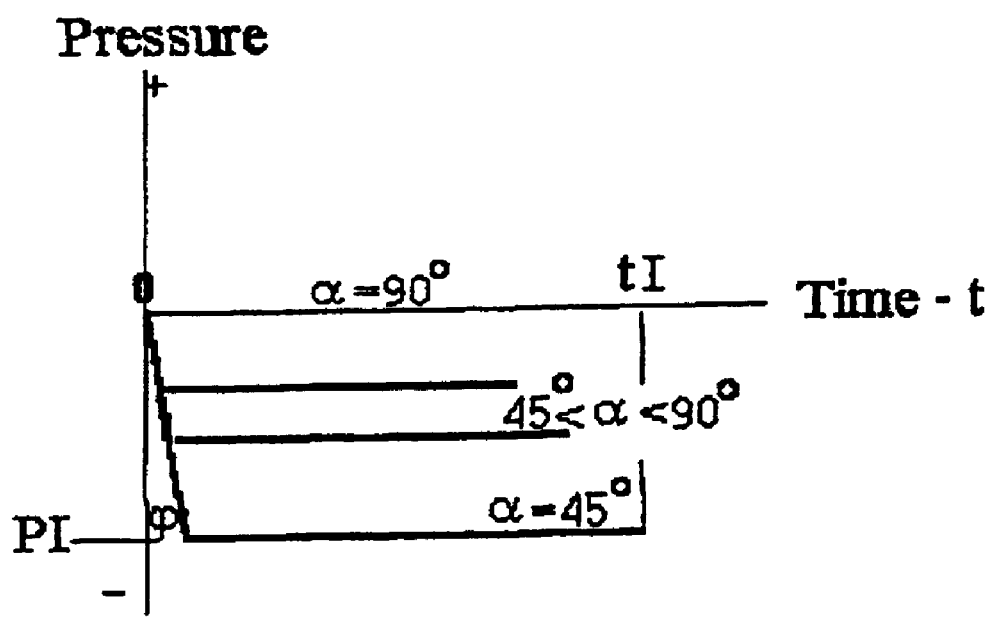
FIG. 13 is a diagram showing yet another operation mode of the preferred system.

FIG. 13 shows the vacuum mode, to increase Lung Volume (Patient breathes easier).

CONCLUSION

Thus, the preferred system and method provides versatile modulation of fluid flow to effect substantial pressure variations. Alternative systems may effect substantial volumetric flow.

Additional advantages and modifications will readily occur to those skilled in the art. The invention in its broader aspects is therefore not limited to the specific details, representative apparatus, and illustrative examples shown and described. Accordingly, departures may be made from such details without departing from the spirit or the scope of Applicants' general inventive concept. The invention is defined in the following claims.

What is claimed is:

1. In a system including a compartment and a person in contact with the compartment having an interior, an artificial respiration system comprising:
    a device for moving fluid, the device including a fluid exit port and a fluid entrance port;
    a first housing defining a first hole in communication with the exit port, a second hole in communication with the interior of the compartment, a third hole in communication with the entrance port, and a fourth hole;
    a second housing in the first housing, the second housing defining a first chamber with a first hole, and a second hole, and a second chamber with a third hole, and a fourth hole;
    a driver mechanically coupled to the second housing, to vary the angular displacement of the second housing relative to the first housing;
    a user interface for generating a first signal indicating a first pressure, a second signal indicating a second pressure, and a third signal indicating a period; and
    a controller that generates a driver control signal, the driver being responsive to the driver control signal, the controller generating the driver control signal to cause the driver to effect a first angular displacement of the second housing depending on the first signal, and to effect a second angular displacement of the second housing depending on the second signal, wherein the second hole of the first housing is substantially perpendicular to the first hole of the first housing, and the fourth hole of the first housing is substantially perpendicular to the third hole of the first housing.

2. The artificial respiration system of claim 1 wherein an extent of overlap of the first hole of the second housing with the first hole of the first housing is a function of the angular displacement of the second housing.

3. The artificial respiration system of claim 1 wherein an extent of overlap of the first hole of the second housing with the first hole of the first housing is a function of the angular displacement of the second housing, and an extent of overlap of the second hole of the second housing with the second hole of the first housing is the function.

4. The artificial respiration system of claim 1 wherein
    an extent of overlap of the first hole of the second housing with the first hole of the first housing is a first function of the angular displacement of the second housing, an extent of overlap of the second hole of the second housing with the second hole of the first housing is the first function,
    an extent of overlap of the third hole of the second housing with the third hole of the first housing is a second function of the angular displacement of the second housing, and an extent of overlap of the fourth hole of the second housing with the fourth hole of the first housing is the second function.

5. The respiration system of claim 4 wherein the first and second functions are substantially the same.

6. The artificial respiration system of claim 1 further including a pressure sensor that generates a pressure signal, wherein the controller generates the driver control signal in response to the pressure signal.

7. The artificial respiration system of claim 1 wherein the controller generates a variable power signal for the device for moving fluid.

8. The artificial respiration system of claim 1 wherein the controller generates a variable power signal for the device for moving fluid, in response to the first signal.

9. In a system including a compartment and a person in contact with the compartment having an interior, an artificial respiration system comprising:
    a device for moving fluid, the device including a fluid exit port and a fluid entrance port;
    a first housing defining a first hole in communication with the exit port, a second hole in communication with the interior of the compartment, a third hole in communication with the entrance port, and a fourth hole;
    a second housing in the first housing, the second housing defining a first chamber with a first hole, and a second hole, and a second chamber with a third hole, and a fourth hole;
    a driver mechanically coupled to the second housing, to vary the angular displacement of the second housing relative to the first housing;
    a user interface for generating a first signal indicating a first pressure, a second signal indicating a second pressure, and a third signal indicating a period; and
    a controller that generates a driver control signal, the driver being responsive to the driver control signal, the controller generating the driver control signal to cause the driver to effect a first angular displacement of the second housing depending on the first signal, and to effect a second angular displacement of the second housing depending on the second signal, wherein the third hole of the first housing is substantially perpendicular to the second hole of the first housing, and the first hole of the first housing is substantially perpendicular to the fourth hole of the first housing.

10. In a system including a compartment and a person in contact with the compartment having an interior, an artificial respiration system comprising:
    a device for moving fluid, the device including a fluid exit port and a fluid entrance port;
    a first housing defining a first hole in communication with the exit port, a second hole in communication with the interior of the compartment, a third hole in communication with the entrance port, and a fourth hole;
    a second housing in the first housing, the second housing defining a first chamber with a first hole, and a second hole, and a second chamber with a third hole, and a fourth hole;
    a driver mechanically coupled to the second housing, to vary the angular displacement of the second housing relative to the first housing;
    a user interface for generating a first signal indicating a first pressure, a second signal indicating a second pressure, and a third signal indicating a period; and
    a controller that generates a driver control signal, the driver being responsive to the driver control signal, the controller generating the driver control signal to cause the driver to effect a first angular displacement of the second housing depending on the first signal, and to effect a second angular displacement of the second housing depending on the second signal, wherein the second hole of the second housing is substantially perpendicular to the first hole of the second housing, and the fourth hole of the second housing is substantially perpendicular to the third hole of the second housing.

11. In a system including a compartment and a person in contact with the compartment having an interior, an artificial respiration system comprising:

a device for moving fluid, the device including a fluid exit port and a fluid entrance port;

a first housing defining a first hole in communication with the exit port, a second hole in communication with the interior of the compartment, a third hole in communication with the entrance port, and a fourth hole;

a second housing in the first housing, the second housing defining a first chamber with a first hole, and a second hole, and a second chamber with a third hole, and a fourth hole;

a driver mechanically coupled to the second housing, to vary the angular displacement of the second housing relative to the first housing;

a user interface for generating a first signal indicating a first pressure, a second signal indicating a second pressure, and a third signal indicating a period; and a controller that generates a driver control signal, the driver being responsive to the driver control signal, the controller generating the driver control signal to cause the driver to effect a first angular displacement of the second housing depending on the first signal, and to effect a second angular displacement of the second housing depending on the second signal, wherein the third hole of the second housing is substantially perpendicular to the second hole of the second housing, and the first hole of the second housing is substantially perpendicular to the fourth hole of the second housing.

12. In a system including a compartment and a person in contact with the compartment having an interior, an artificial respiration system comprising:

a device for moving fluid, the device including a fluid exit port and a fluid entrance port;

a first housing defining a first hole in communication with the exit port, a second hole in communication with the interior of the compartment, a third hole in communication with the entrance port, and a fourth hole;

a second housing in the first housing, the second housing defining a first chamber with a first hole, and a second hole, and a second chamber with a third hole, and a fourth hole;

a driver mechanically coupled to the second housing, to vary the angular displacement of the second housing relative to the first housing;

a user interface for generating a first signal indicating a first pressure, a second signal indicating a second pressure, and a third signal indicating a period; and a controller that generates a driver control signal, the driver being responsive to the driver control signal, the controller generating the driver control signal to cause the driver to effect a first angular displacement of the second housing depending on the first signal, and to effect a second angular displacement of the second housing depending on the second signal, wherein D is a diameter defined by the second housing and d is a diameter defined by the first hole in the second housing, and D is approximately equal to $d/\sin(\pi/8)$.

13. In a system including a compartment and a person in contact with the compartment having an interior, an artificial respiration system comprising:

a device for moving fluid, the device including a fluid exit port and a fluid entrance port;

a first housing defining a first hole in communication with the exit port, a second hole in communication with the interior of the compartment, a third hole in communication with the entrance port, and a fourth hole;

a second housing in the first housing, the second housing defining a first chamber with a first hole, and a second hole, and a second chamber with a third hole, and a fourth hole;

a driver mechanically coupled to the second housing, to vary the angular displacement of the second housing relative to the first housing;

a user interface for generating a first signal indicating a first pressure, a second signal indicating a second pressure, and a third signal indicating a period; and a controller that generates a driver control signal, the driver being responsive to the driver control signal, the controller generating the driver control signal to cause the driver to effect a first angular displacement of the second housing depending on the first signal, and to effect a second angular displacement of the second housing depending on the second signal, wherein d2 is a diameter defined by the first hole in the second housing, and d1 is a diameter defined by the first hole in the first housing, and $d2 \geq d1$.

* * * * *